United States Patent [19]
Pavanasasivam

[11] Patent Number: 4,744,981
[45] Date of Patent: May 17, 1988

[54] TRICHOTHECENE ANTIBODY CONJUGATES

[75] Inventor: Gowsala Pavanasasivam, Edmonds, Wash.

[73] Assignee: NeoRx Corporation, Seattle, Wash.

[21] Appl. No.: 788,325

[22] Filed: Oct. 17, 1985

[51] Int. Cl.$^4$ ............................................. A61K 39/395
[52] U.S. Cl. ..................... 424/85; 436/547; 436/548; 530/387; 530/388; 530/389; 530/390; 530/391
[58] Field of Search ........................ 530/387, 389, 390; 436/547; 424/85

[56] References Cited

U.S. PATENT DOCUMENTS 4,507,234  3/1985  Kato et al. ........................... 530/389
4,618,585 10/1986  Chan ................................... 530/387
4,624,846 11/1986  Goldenberg .......................... 530/387

FOREIGN PATENT DOCUMENTS

EP88695  7/1983  European Pat. Off. .

OTHER PUBLICATIONS

Hunter et al, Chem. Abst., vol. 102 (1985), p. 76957n.
Cha et al, Chem. Abst., vol. 101 (1984), pp. 228, 260z.
Bamburg, J. R., "Biological and Biochemical Actions of Trichothecene Mycotoxins", *Prog. Molec. Subcell. Biol.*, 8:41–110, 1983.
Uhr, J. W., "Immunotoxins: Harnessing Nature's Poisons", *J. Immuno.*, 133:i–x, 1984.
Foxwell, B. M., "Monoclonal Antibody-Toxin Conjugates as Selective Cytotoxic Agents", *Immunotoxicology*, Academic Press, London, pp. 359–368, 1983.
"Protection Against Trichothecene Mycotoxins", 1983, National Academy Press, Washington, D.C., pp. 17–20; 129–136.

*Primary Examiner*—Sam Rosen
*Attorney, Agent, or Firm*—Seed and Berry

[57] ABSTRACT

Conjugates of trichothecenes and agents that bind to a defined population of cells are disclosed. Preferred are conjugates of trichothecene molecules with polyclonal or monoclonal antibodies or fragments thereof that recognize antigens that are present only on tumor cells or are augmented in their expression on tumor cells as compared to normal tissues. Trichothecene molecules are coupled to the agent through non-covalent and covalent linkages, such as peptide bonds, disulfide bonds, thioester bonds, or thioether bonds. A method for inhibiting the growth and metabolism of antigen-positive cells is also disclosed.

21 Claims, No Drawings

4,744,981

TRICHOTHECENE ANTIBODY CONJUGATES

TECHNICAL FIELD

The present invention relates generally to the conjugation of molecules to agents that bind to a defined population of cells and more specifically, to conjugates of agents such as antibodies with trichothecenes and to methods for using these conjugates.

BACKGROUND ART

The use of antibodies as carriers for toxic agents to skill tumor cells selectively has depended upon the coordination of research in three distinct areas: (a) the develoment of polyclonal or monoclonal antibodies (and their fragments) with specificity for a defined population of cells, such as tumor cells; (b) the elucidation of the chemistry of toxic molecules and the conditions appropriate for their linkage to antibodies; and (c) the production and isolation of naturally occurring toxic molecules. Conjugates of monoclonal antibodies with drugs, plant toxins, and ribosomal inactivating proteins have been summarized by Morgan and Foon, (Monoclonal Antibody Therapy of Cancer: Preclinical Models and Investigations; *Basic and Clinical Tumor Immunology*, Vol. 2, Kluwer Academic Publishers, Hingham, MA) and Uhr (*Journal of Immunology* 133: i–vii, 1984). Interest in the potent higher plant toxin molecules peaked with the development of monoclonal antibodies because it appeared that the latter could be used as highly specific targeting agents for these toxins.

In general, the higher molecular weight toxins have characteristic A and B chains, with the B chain responsible for binding (usually via lectins to oligosaccharides) and A chains that act catalytically to irreversibly inhibit elongation factor 2 (EF2), therefore preventing protein synthesis. The vision was that the specificity of the antibody could substitute for the non-specific binding of B chain and deliver A chain selectively to tumor cells. More recently, a class of compounds called "ribosomal inactivating proteins" (RIPs) have been discovered that represent the equivalent of A chains without any associated B chain.

A number of obstacles emerged, however, that compromised the realization of this simple vision. First, it was apparent that it was critical to develop systems to remove B chain from A chain beyond purity achieved with simple affinity chromatography. The RIPs and cloned toxins represent one practical solution to this problem. Second, the reticuloendothelial system remove macromolecules from the circulation, especially those that have been altered, such an as antibody that has been bound to toxin. Third, it became apparent that there were receptors for the carbohydrates that exist naturally on the protein plant toxins. These also contributed to non-specific uptake and, therefore, toxicity. Finally, it became clear that B chain was critical for more than just binding to the cell, and seemed to facilitate the translocation of the A chain into the cell and eventually into the cytoplasm, where it effected its cytotoxicity.

Due to these obstacles, there is a need in the art for a class of conjugates that overcome the problems noted above, while concurrently possessing the capability of killing defined populations of cells, such as tumor cells, on a selective basis. The present invention fulfills this need and further provides other related advantages.

DISCLOSURE OF INVENTION

Briefly stated, the present invention discloses conjugates of trichothecenes and agents that bind to a defined population of cells. Preferred are conjugates of trichothecene molecules with polyclonal or monoclonal antibodies or fragments thereof that recognize antigens that are present only on tumor cells or are augmented in their expression on tumor cells as compared to normal tissues.

In accordance with the present invention, "trichothecenes" are defined to include molecules derived from *Fungi imperfecti*, *Baccharus megapotamica* or prepared synthetically or synthesized from fungal products that have as their common characteristic a sesquiterpenoid central ring structure and its simple and macrocyclic derivatives.

The trichothecene molecules are coupled to the agent through non-covalent and covalent linkages, preferably a covalent linkage, such as a peptide bond, a disulfide bond, a thioester bond, or a thioether bond. This covalent linkage may be formed between: (a) a trichothecene hemisuccinate carboxylic acid; (b) a trichothecene hemisuccinate N-hydroxy succinimidate ester, or (c) trichothecene/poly-L-lysine complexes, or any polymeric carrier, and one or more amino groups of the agent.

A related aspect of the present invention is directed toward a method for inhibiting the growth and metabolism of antigen positive cells, comprising exposing the antigen positive cells to a conjugate of a trichothecene and an agent that binds to the antigen positive cells.

Other aspects of the invention will become relevant upon reference to the following detailed description.

BEST MODE FOR CARRYING OUT THE INVENTION

"Trichothecenes" are a species of mycotoxins produced by soil fungi of the class *Fungi imperfecti* or isolated from *Baccharus megapotamica* (Bamburg, J. R., *Proc. Molec. Subcell Bio.* 8: 41–110, 1983; Jarvis & Mazzola, *Acc. Chem. Res.* 15: 338–395, 1982). They appear to be the most toxic molecules that contain only carbon, hydrogen and oxygen (Tamm, C. *Fortschr. Chem. Org. Naturst.* 31: 61–117, 1974). They all act at the level of the ribosome as inhibitors of protein synthesis, either at the initiation, elongation or termination phases. As small molecules (ca. 4–600 m.w.), they have potential advantages:

(1) improved delivery due to only minor changes in the molecular weight of antibody;

(2) lack of receptor mediated, non-specific uptake, e.g., via carbohydrate receptors, a drawback of higher molecular weight (ca. 30,000 m.w.) plant toxins, like ricin A chain, or ribosomal inactivating proteins such as gelonin.

Similar to toxins, however, mycotoxins can be extremely potent. They are the most potent small molecule inhibitors of protein synthesis in eucaryotic cells. Unconjugated to antibody, verrucarin A (Table 4) is 10-fold or greater more potent than antinomycin D, the most potent per weight of the chemotherapeutic drugs currently approved for clinical use. Since most currently used drugs act at the level of DNA, these ribosomal inactivating drugs, like toxins, should not be adversely affected by resistance to "standard" drugs, and should produce additive cytotoxicity to existing therapies.

There are two broad classes of trichothecenes: those that have only a central sesquiterpenoid structure and those that have an additional macrocyclic ring (simple and macrocyclic trichothecenes, respectively). The simple trichothecenes may be subdivided into three groups. Group A simple trichothecenes may be characterized by the formula:

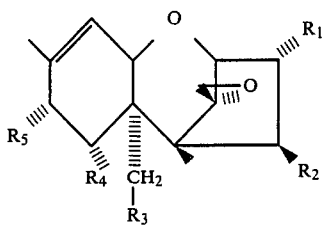

wherein $R_1$ is H, OH, or

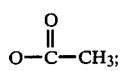

$R_2$ is H, OH, or 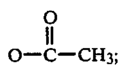 $R_3$ is H, OH, or 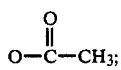 $R_4$ is H or OH; and $R_5$ is H,

OH, 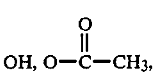  or

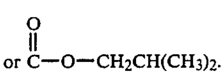

Representative Group A simple trichothecenes and corresponding functional groups are listed in Table 1.

TABLE 1

| Group A Simple Trichothecenes | | | | | |
|---|---|---|---|---|---|
| Trichothecenes | $R_1$ | $R_2$ | $R_3$ | $R_4$ | $R_5$ |
| Trichothecene (scirpene) | H | H | H | H | H |
| Trichodermol (roridin C) | H | OH | H | H | H |
| Dihydrotrichothecene | H | H | OH | H | OH |
| Scirpen-4,8-diol | H | OH | H | H | OH |
| Verrucarol | H | OH | OH | H | H |
| Scirpentriol | OH | OH | OH | H | H |
| T-2 tetraol | OH | OH | OH | H | OH |
| Pentahydroxyscirpene | OH | OH | OH | OH | OH |
| 4-Deacetylneosolaniol | OH | OH | OH | H | OH |
| Trichodermin | H | OAc | H | H | H |
| Deacetylcalonectrin | OAc | H | OH | H | H |
| Calonectrin | OAc | H | OAc | H | H |
| Diacetylverrucarol | H | OAc | OAc | H | H |
| 4-Monoacetoxyscirpenol | OH | OAc | OH | H | H |
| 4,15-Diacetoxyscirpenol (DAS) | OH | OAc | OAc | H | H |
| 7-Hydroxydiacetoxyscirpenol | OH | OAc | OAc | OH | H |
| 8-Hydroxydiacetoxyscirpenol (neosolaniol) | OH | OAc | OAc | H | OH |
| 7,8-Dihydroxydiacetoxyscirpenol | OH | OAc | OAc | OH | OH |
| 7-Hydroxy-8-acetyldiacetoxyscirpenol | OH | OAc | OAc | OH | OAc |
| 8-Acetylneosolaniol (8-Acetyl-DAS) | OH | OAc | OAc | H | OAc |
| NT-1 | OH | OAc | OH | H | OAc |
| NT-2 | OH | OAc | OH | H | OH |
| HT-2 toxin | OH | OH | OAc | H | $OCOCH_2—CH(CH_3)_2$ |
| T-2 toxin | OH | OAc | OAc | H | $OCOCH_2—CH(CH_3)_2$ |
| Acetyl T-2 toxin | OAc | OAc | OAc | H | $OCOCH_2—CH(CH_3)_2$ |

Group B simple trichothecenes may be characterized by the formula:

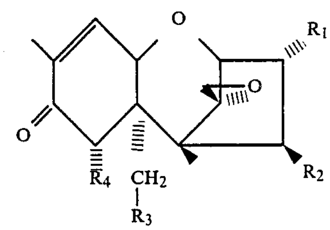

wherein $R_1$ is H, OH, or 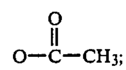 $R_2$ is H, OH, or or $R_3$ is H, OH, or 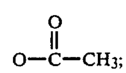 and $R_4$ is H, OH, or 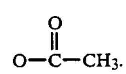 Representative Group B simple trichothecenes and corresponding functional groups are listed in Table 2.

TABLE 2

| Group B Simple Trichothecenes | | | | |
|---|---|---|---|---|
| Trichothecenes | $R_1$ | $R_2$ | $R_3$ | $R_4$ |
| Trichothecolone | H | OH | H | H |
| Trichothecin | H | $OCOCH=CHCH_3$ | H | H |
| Deoxynivalenol (DON) | OH | H | OH | OH |
| 3-Acetyldeoxynivalenol | OAc | H | OH | OH |
| 5-Acetyldeoxynivalenol | OH | H | OH | OAc |
| 3,15-Diacetyldeoxynivalenol | OAc | H | OAc | OH |
| Nivalenol | OH | OH | OH | OH |
| 4-Acetylnivalenol (fusarenon-X) | OH | OAc | OH | OH |
| 4,15-Diacetylnivalenol | OH | OAc | OAc | OH |

TABLE 2-continued
Group B Simple Trichothecenes

| Trichothecenes | R₁ | R₂ | R₃ | R₄ |
|---|---|---|---|---|
| 4,7,15-Triacetylnivalenol | OH | OAc | OAc | OAc |
| Tetracetylnivalenol | OAc | OAc | OAc | OAc |

Group C simple trichothecenes may be characterized by the formula:

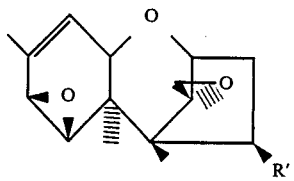

wherein
R' is OH or

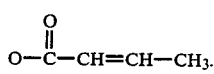

Representative Group C simple trichothecenes and corresponding R' functional groups are listed in Table 3.

TABLE 3
Group C Simple Trichothecenes

| Trichothecenes | R' |
|---|---|
| Crotocol | OH |
| Crotocin | OCOCH=CHCH₃ |

The macrocyclic trichothecenes may be characterized by the formula:

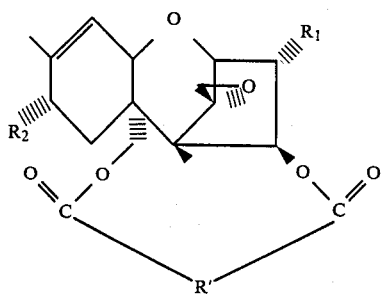

wherein
R₁ is OH or

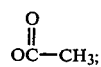

R₂ is H, OH,

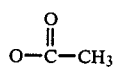

or OCOCH₂CH(CH₃)₂; and
R' is:

TABLE 4

| R' | Representative Macrocyclic Trichothecenes |
|---|---|
| —CHOHCHMeCH₂CH₂OCCH=CHCH=CH— (C=O) | Verrucarin A |
| —CHCMeCH₂CH₂OCCH=CHCH=CH— (epoxide, C=O) | Verrucarin B |
| —CH=CMeCH₂CH₂OCCH=CHCH=CH— (C=O) | Verrucarin J (Satratoxin C) |
| —CCHMeCH₂CH₂OCCH=CHCH=CH— (C=O, C=O) | 2-Dehydro-verrucarin A |
| —CHOHCHMeCH₂CH₂OCHCH=CHCH=CH— with MeCHOH | Roridin A |
| —CHCMeCH₂CH₂OCHCH=CHCH=CH— (epoxide) with MeCHOH | Roridin D |
| —CH=CMeCH₂CH₂OCHCH=CHCH=CH— with MeCHOH | Roridin E (Satratoxin D) |
| —CH=CHMeCH₂CH (O-CH=CHCH=CHCH—)Me | Roridin H |
| —HC (O, OH) — CH=CHCH=CH— with CHOCH₃ | Satratoxin F |
| —HC (O, OH) — CH=CHCH=CH— with CH(CH₃)OH | Satratoxin G |
| —CH= (O, OH) — CH=CHCH=CH— with CH(CH₃)OH | Satratoxin H |
| —CH= (O, H, OH, H) — CH₂CH₂CH=CH— | Vertisporin |

The sesquiterpenoid ring functions in a manner similar to the A chains of plant toxins, in binding to ribosomes and inhibiting protein synthesis. The macrocyclic ring enhances cell binding and internalization in an unknown manner. There are molecules in each class that, while potent inhibitors of translation in cell-free systems, are only minimally cytotoxic ($ID_{50}$ 10 ug/ml) to eucaryotic cells.

Variations in ribosome binding ability are not well correlated with cytotoxicity, strongly suggesting that differential delivery to ribosomes in the cell or intracellular deactivation may play an important role in the activities of these drugs against eucaryotic cells. (Bamburg, J. R., Biological and Biochemical Actions of Trichothecene Mycotoxins, *Prog. Mol. Subcell. Biol.* 8: 41–110, 1983; McLaughlin, C. S., Vaughan, M. H., Cambell, I. M., Wei, C. M., Stafford, M. E., and Hansen, B. S., Inhibition of Protein Synthesis by Trichothecenes, In: *Mycotoxins in Human and animal Health*, Pathotox Publishers, Park Forest South, IL, pp. 263–273, 1977; and Doyle, T. W., and Bradner, W. T., Trichothecenes, In: *Anticancer Agents Based on Natural Product Models* [Cassidy and Bouros, Eds.] Academic Press, Inc., New York, NY, pp. 43–72, 1980.) It is possible, for example, that verrucarol binds poorly to cell membranes, or may be deactivated intracellularly, deficiencies that may be overcome by conjugation to monoclonal antibodies. There have been some studies of the rates at which certain of the trichothecenes are converted into biologically inactive molecules (apotrichothecenes) by intracellular acid catalysis as might occur in lyzosomes. The macrocyclic trichothecenes and some simple trichothecenes such as anguidine and T-2 toxin are inactivated quite slowly, whereas less cytotoxic molecules, such as verrucarol, are inactivated more quickly. There is an inverse linear correlation between cytotoxicity and the rate of this rearrangement into apotrichothecenes.

Anguidine, a simple trichothecene, has been tested in Phase I (Murphy, W. K., Burgess, M. A., Valdivieso, M., Livingston, R. B., Bodey, G. P., and Freireich, E. J., Phase I Evaluation of Anguidine, *Cancer Treat. Repts.* 62: 1497, 1978) and Phase II (Adler, S. S., Lowenbraun, S., Birch, B., Jarrell, R., and Garrerd, J., Anguidine: A Broad Phase II Study of the Southeastern Cancer Study Group, *Cancer Treat. Repts.* 68: 423, 1984) clinical trials in patients. The overall tumor response rate was low and there was considerable hematologic toxicity in the Phase II trial. In the Phase I trial, toxicity included nausea, vomiting, hypotension, central nervous system symptoms, diarrhea, chills and fever, generalized burning erythema, stomatitis, shortness of breath, moderate myelosuppression with an association between life threatening toxicity and the presence of liver metastases or impairment of liver function recognized at higher doses.

The linkage of trichothecene molecules to polyclonal and monoclonal antibodies or fragments thereof that recognize antigens that are augmented in their expression on tumor cells as compared to normal tissues may be divided into two distinct strategies: (1) linking poorly-cytotoxic trichothecenes to antibodies or fragments thereof in order to render them cytotoxic; and (2) conjugating cytotoxic trichothecenes to antibodies or fragments thereof to deliver them selectively to tumor cells, sparing normal tissues most of their toxicity.

Within the present invention, monoclonal antibodies were prepared by immunizing rodents or other animals and/or are developed by harvesting human lymphocytes from patients bearing malignancies and immortalizing the antibody secretion of the cells by standard hybridoma technology (Geffer et al., *Somatic Cell Genet.* 3: 231, 1977). Alternatively, polyclonal antiserum is prepared by harvesting serum from animals following immunization with tumor cells or other defined tumor-associated antigens or harvesting from humans who have or have had exposure to tumors or tumor-associated antigens, and subjecting the serum to standard purification techniques. Antibodies were screened for specificity using standard radioimmunoassay or enzyme-linked immunosorbent assay (ELISA) against the appropriate targets. Screening was performed with normal human tissues to select antibody with appropriate tumor specificity.

After purification of the desired antibody species, the antibodies were conjugated to the trichothecene molecules. The carboxylic acid of the trichothecene hemisuccinate was linked to the amino groups of the antibody using a carbodiimide. Alternatively, N-hydroxy succimidate ester of the trichothecene hemisuccinate is prepared and used to link to the amino groups of the antibody. Both of these methods result in an amide bond between the trichothecene and the antibody. Thioether can also be used as a stable bond between the antibody and the trichothecene. In addition, the trichothecene molecules are linked to poly-L-lysine (m.w. 300 to 150,000). The poly-L-lysine/trichothecene complex is then linked to the antibody via an amide bond. Also, when a more labile bond seems desirable, the trichothecene is linked by a disulfide or a thioester bond to the monoclonal antibody (MA).

The immunoconjugates were easily separated from the unreacted trichothecene by FPLC gel filtration using a TSK 3000 column. Alternatively, the unreacted trichothecene is removed by dialysis.

The molecular weight of the conjugate will not be significantly greater than that of the free antibody. Therefore, separation of the immunoconjugate from free antibody requires use of hydroxylapatite or hydrophobic column chromatography.

Conjugates were analyzed by isoelectric focusing (IEF) and SDS-PAGE. IEF is a measure of the degree of substitution and resulting charge of the antibody. SDS-PAGE separates proteins on the basis of molecular weight and is used to assess the covalent aggregates formed during the conjugation process. The conjugate is compared to the unconjugated antibody for immune reactivity that is quantified by flow cytometry. The immunoconjugates are incubated with antigen positive cells, washed, and then the cells are incubated with fluorescein isothiocyanate-linked goat antimouse antibody. Cell bound fluorescence is read on a flow cytometer and mean fluorescence index is calculated. Competition of performed using a standard unconjugated antibody preparation in comparison for inhibition with the conjugate. Similar analyses, employing antigen negative cells, were used to demonstrate the retention of specificity of the conjugate for antigen positive cells.

Cytotoxicity of the immunoconjugates was assessed with two methods. A colorimetric assay employs 3-(4,5-dimethylthiazol-2-yl)-2,5-diphenyl tetrozolium bromide as the substrate. This substance is cleaved by living cells to yield a dark blue formazan product. This process requires active mitochondria. The substrate (MTT) was solubilized and read on an ELISA reader. This assay has an excellent correlation with the standard $^3$H-thymidine incorporation assay and avoids the use of radioactivity. $^3$H-thymidine was reserved for confirmation of major results.

Potency and selectivity assays were performed by incubating conjugates with antigen positive and antigen negative cell lines. Conjugates were added to the cells at varying concentrations and cell survival assessed after continuous and short exposure times. The conjugates were incubated with the cells for three days for continuous exposure and for two hours for the short exposure. At the end of three days cell survival was assessed.

The conjugates were also tested for their ability to inhibit peptidyl transferase. The assay is based upon competition with radiolabeled trichodermin for the binding site on the 60S ribosome. Conjugates were also tested for their ability to inhibit protein synthesis using natural mRNA to determine their overall effect on protein synthesis and a poly U to measure the effect on elongation.

To summarize the examples which follow, Example I illustrates the use of an antibody conjugate to render a poorly-cytotoxic molecule toxic to eucaryotic cells, and Example II illustrates the use of an antibody to render a generally cytotoxic molecule specifically toxic to antigen positive cells.

The following examples are offered by way of illustration and not by way of limitation.

EXAMPLE I

Verrucarol

Verrucarol is a simple, poorly cytotoxic trichothecene. It is conjugated to anti-melanoma antibody 9.2.27 using a carbodiimide. The primary or secondary hydroxyl group react with the carbodiimide to form an active form of the molecule. This molecule then reacts with lysines on the antibody to form the conjugate. Titration of the conjugate against antigen positive and antigen negative melanoma cells indicated an $ID_{50}$ of $10^{-8}$M. This is compared to the drug verrucarol alone that has an $ID_{50}$ of $10^{-5}$M or greater.

EXAMPLE II

Verrucarin A

Verrucarin A or its hemisuccinate is conjugated to monoclonal antibody 9.2.27 by the same method as stated in Example 1. Increasing titers of the conjugate are incubated with the antigen positive and antigen negative melanoma cells and then tested for potency and selectivity as described herein. The $ID_{50}$ against the antigen positive cells was $10^{-7}$M or better where there was no toxicity against the antigen negative cells. Verrucarin A itself yielded an $ID_{50}$ of $2.5 \times 10^{-11}$M.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

I claim:

1. A conjugate of a trichothecene and an antibody or antibody fragment, said antibody or antibody fragment being capable of specifically binding to a defined population of cells.

2. The conjugate of claim 1 wherein said trichothecene has a central sesquiterpenoid structure.

3. The conjugate of claim 2 wherein said trichothecene has an additional macrocyclic ring.

4. The conjugate of claim 2 wherein said trichothecene is selected from the group consisting of trichodermol, verrucarol, trichodermin, anguidine, and T-2 toxin.

5. The conjugate of claim 3 wherein said trichothecene is selected from the group consisting of verrucarin A, verrucarin B, verrucarin J, 2'-dehydroverrucarin A, roridin A, roridin D, roridin E, roridin H, satratoxin F, satratoxin G, satratoxin H, vertisporin, and baccharins.

6. The conjugate of claim 1 wherein the trichothecene is verrucarol.

7. The conjugate of claim 1 wherein the trichothecene is verrucarin A.

8. The conjugate of claim 1 wherein said trichothecene mycotoxin comprises the formula:

wherein:

$R_1$ is H, OH, or $$O-\overset{O}{\underset{\|}{C}}-CH_3;$$

$R_2$ is H, OH, $$O-\overset{O}{\underset{\|}{C}}-CH_3 \text{ or } \overset{O}{\underset{\|}{C}}OCH=CHCH_3;$$

$R_3$ is H, OH, or $$O-\overset{O}{\underset{\|}{C}}-CH_3$$

$R_4$ is H, OH, =O, $$O-\overset{O}{\underset{\|}{C}}-CH_3, \text{ or } \overset{O}{\underset{\|}{C}}OCH_2CH(CH_3)_2.$$

9. The conjugate of claim 8 wherein $R_4$ comprises an epoxide group.

10. The conjugate of claim 1 wherein said trichothecene comprises the formula:

wherein:

$R_1$ is OH, or $R_2$ is H, OH, $$O-\overset{\overset{O}{\|}}{C}-CH_3$$

$$O-\overset{\overset{O}{\|}}{C}-CH_3,$$

or OCOCH$_2$CH(CH$_3$)$_2$; and
R' is:

$$-CHOHCHMeCH_2CH_2O\overset{\overset{O}{\|}}{C}CH=CHCH=CH-$$

$$-\underset{\underset{O}{\diagdown\diagup}}{CHCMe}CH_2CH_2O\overset{\overset{O}{\|}}{C}CH=CHCH=CH-$$

$$-CH=CMeCH_2CH_2O\overset{\overset{O}{\|}}{C}CH=CHCH=CH-$$

$$-\overset{\overset{O}{\|}}{C}CHMeCH_2CH_2O\overset{\overset{O}{\|}}{C}CH=CHCH=CH-$$

$$-CHOHCHMeCH_2CH_2O\underset{\underset{MeCHOH}{|}}{CH}CH=CHCH=CH-.$$

11. The conjugate of claim 1 wherein said antibody comprises monoclonal antibodies.

12. The conjugate of claim 11 wherein the monoclonal antibodies are of human or other warm blooded animal origin.

13. The conjugate of claim 1 wherein said antibody comprises polyclonal antibodies.

14. The conjugate of claim 1 wherein said defined population of cells comprises tumor cells.

15. The conjugate of claim 1 wherein said defined population of cells comprises cells bearing tumor-associated antigens.

16. The conjugate of claim 1 wherein said trichothecene and said antibody or antibody fragment are coupled through a covalent linkage.

17. The conjugate of claim 16 wherein the covalent linkage is formed between a trichothecene hemisuccinate carboxylic acid and one or more amino groups of the antibody or antibody fragment.

18. The conjugate of claim 16 wherein said covalent linkage is formed between a trichothecene hemisuccinate N-hydroxy succinimidate ester and one or more amino groups of the antibody or antibody fragment.

19. The conjugate of claim 16 wherein said covalent linkage is formed between trichothecene/poly-L-lysine complexes and one or more amino groups of the antibody or antibody fragment.

20. The conjugate of claim 16 wherein said covalent linkage is a disulfide bond, thioester bond, or thioether bond.

21. A method for inhibiting antigen positive cells, comprising:
    exposing the antigen positive cells to a conjugate of a trichothecene and an antibody or antibody fragment specific for said antigen positive cells.

* * * * *